(12) United States Patent
Wang et al.

(10) Patent No.: US 10,500,609 B2
(45) Date of Patent: Dec. 10, 2019

(54) PROCESS FOR COATING OF ARTICLES

(71) Applicant: Master Dynamic Limited, Shatin, New Territories, Hong Kong (CN)

(72) Inventors: Yingnan Wang, Hong Kong (CN); Zhuonan Miao, Hong Kong (CN); Ching Tom Kong, Hong Kong (CN); Woon Ming Lau, Hong Kong (CN); Sui Kong Hark, Hong Kong (CN); Ka Wai Wong, Hong Kong (CN)

(73) Assignee: MASTER DYNAMIC LIMITED, Shatin, New Territories, Hong Kong (CN)

( * ) Notice: Subject to any disclaimer, the term of this patent is extended or adjusted under 35 U.S.C. 154(b) by 0 days.

(21) Appl. No.: 15/736,776

(22) PCT Filed: Jun. 17, 2016

(86) PCT No.: PCT/CN2016/086282
§ 371 (c)(1),
(2) Date: Dec. 15, 2017

(87) PCT Pub. No.: WO2016/202300
PCT Pub. Date: Dec. 22, 2016

(65) Prior Publication Data
US 2018/0169696 A1    Jun. 21, 2018

(30) Foreign Application Priority Data

Jun. 17, 2015   (HK) .................................. 15105780

(51) Int. Cl.
*B05D 1/00* (2006.01)
*B05D 1/38* (2006.01)
(Continued)

(52) U.S. Cl.
CPC ............... *B05D 1/38* (2013.01); *A01N 33/12* (2013.01); *A01N 37/02* (2013.01); *A01N 43/16* (2013.01);
(Continued)

(58) Field of Classification Search
CPC .... C08J 3/00; C03J 7/00; C23C 16/00; B05D 1/00; A01N 43/00
See application file for complete search history.

(56) References Cited

U.S. PATENT DOCUMENTS

2008/0269186 A1* 10/2008 Bignozzi .............. C07D 213/79
                                                                    514/185
2012/0056167 A1*  3/2012 Lau ........................... C08J 7/04
                                                                    257/40
(Continued)

FOREIGN PATENT DOCUMENTS

CN       102414260 A    4/2012
CN       103304827 A    9/2012
(Continued)

OTHER PUBLICATIONS

Written Opinion and International Search Report of PCT/CN2016/086282.
(Continued)

*Primary Examiner* — Gordon Baldwin
*Assistant Examiner* — Mohammad Mayy
(74) *Attorney, Agent, or Firm* — Joseph G. Chu; JCIP

(57) ABSTRACT

A process of providing an antibacterial coating to the surface of an article including the steps of applying a layer of an antibacterial precursor layer to the surface of an article to which an antibacterial coating is to be applied, wherein said antibacterial precursor layer is a precursor from which the coating is to be formed; and directing a neutral molecular hydrogen flux from a neutral molecular hydrogen flux
(Continued)

emission source towards the surface of the article. Upon impact of neutral hydrogen molecules on molecules at or on the surface of an article, the bonds of the antibacterial precursor layer are selectively ruptured, and wherein the selectively ruptured bonds cross-link with themselves or with other chemical moieties at said surface or a combination thereof, resulting an antibacterial coating being formed on the surface of the article.

17 Claims, 9 Drawing Sheets

(51) Int. Cl.

| | |
|---|---|
| C23C 14/50 | (2006.01) |
| C23C 14/30 | (2006.01) |
| C23C 14/34 | (2006.01) |
| C23C 16/458 | (2006.01) |
| C23C 16/503 | (2006.01) |
| C23C 16/505 | (2006.01) |
| C23C 16/511 | (2006.01) |
| C07C 323/52 | (2006.01) |
| C08J 3/24 | (2006.01) |
| C08J 3/28 | (2006.01) |
| C08J 7/18 | (2006.01) |
| C08L 5/08 | (2006.01) |
| C08L 39/00 | (2006.01) |
| B05D 3/10 | (2006.01) |
| A01N 33/12 | (2006.01) |
| A01N 37/02 | (2006.01) |
| A01N 43/16 | (2006.01) |
| B05D 1/18 | (2006.01) |
| B05D 1/36 | (2006.01) |

(52) U.S. Cl.
CPC ............ *B05D 3/107* (2013.01); *C07C 323/52* (2013.01); *C08J 3/24* (2013.01); *C08J 3/28* (2013.01); *C08J 7/18* (2013.01); *C08L 5/08* (2013.01); *C08L 39/00* (2013.01); *C23C 14/30* (2013.01); *C23C 14/34* (2013.01); *C23C 14/505* (2013.01); *C23C 16/4584* (2013.01); *C23C 16/503* (2013.01); *C23C 16/505* (2013.01); *C23C 16/511* (2013.01); *B05D 1/185* (2013.01); *B05D 1/36* (2013.01); *B05D 2201/02* (2013.01); *B05D 2202/40* (2013.01); *B05D 2203/30* (2013.01); *B05D 2350/60* (2013.01); *B05D 2518/00* (2013.01)

(56) References Cited

U.S. PATENT DOCUMENTS

| 2013/0001204 A1* | 1/2013 | Mistry | H01H 1/24 |
| | | | 219/121.59 |
| 2013/0280647 A1 | 10/2013 | Liu et al. | |
| 2015/0017785 A1 | 1/2015 | Gu et al. | |

FOREIGN PATENT DOCUMENTS

| CN | 104910406 B | 1/2019 |
| EP | 2403979 A1 | 1/2012 |
| WO | 2010099609 A1 | 9/2010 |

OTHER PUBLICATIONS

European Search Report for International Patent Application No. PCT/CN2016/086282.
Extended European Search Report for International Patent Application No. EP16811041.
Justin Gorham et al: "Modification of Alkanethiolate Self-Assembled Monolayers by Atomic Hydrogen: Influence of Alkyl Chain Length", Journal of Physical Chemistry C, vol. 111, No. 1, Jul. 20, 2006 (Jul. 20, 2006), pp. 374-382, XP055601486, ISSN: 1932-7447, DOI: 10.1021/jp0646224 *II. Experimental Section; III. Results; figure 5*.

* cited by examiner

| Antimicrobial Effectiveness Testing | Laboratory I.D. | | HK1539570-002 | | | HK1539570-001 | | | |
|---|---|---|---|---|---|---|---|---|---|
| | Date of Sampling & Testing | | 14/10/2015 | | | 14/10/2015 | | | |
| | SAMPLE IDENTIFICATION | Inoculum control | Antibacterial coating (as treated) on Au/Si | | | Bared Au/Si wafer | | | |
| | Unit | CFU/mL | CFU/mL | % | Nil | CFU/mL | % | Nil | |
| | LOR | 1 | 1 | 0.1 | 0.01 | 1 | 0.1 | 0.01 | |
| | | Initial | 1 hour | 1 hour | % reduction | Log₁₀ reduction | 1 hour | % reduction | Log₁₀ reduction |
| Test Organism Species Escherichia coli (AATCC 25922) | | 270,000 | 260,000 | <1 | >99.9% | >4.71 | 5,100 | 98.0% | 5.41 |

| Antimicrobial Effectiveness Testing | Laboratory I.D. | | HK1539570-005 | | | HK1539570-003 | | | HK1539570-004 | | |
|---|---|---|---|---|---|---|---|---|---|---|---|
| | Date of Sampling & Testing | | 29/10/2015 | | | 29/10/2015 | | | 29/10/2015 | | |
| | SAMPLE IDENTIFICATION | Inoculum control | Bared Au/Si wafer - Ref | | | Antibacterial coating (2000x rub) on Au/Si | | | Antibacterial coating (10000x rub) on Au/Si | | |
| | Unit | CFU/mL | CFU/mL | % | Nil | CFU/mL | % | Nil | CFU/mL | % | Nil |
| | LOR | 1 | 1 | 0.1 | 0.01 | 1 | 0.1 | 0.01 | 1 | 0.1 | 0.01 |
| | | Initial | 1 hour | 1 hour | % reduction | Log₁₀ reduction | 1 hour | % reduction | Log₁₀ reduction | 1 hour | % reduction | Log₁₀ reduction |
| Test Organism Species Escherichia coli (AATCC 25922) | | 170,000 | 160,000 | 140,000 | 12.5% | 4.30 | 93,600 | 42% | 0.23 | 112,000 | 30% | 0.15 |

Figure 2

| Antimicrobial Effectiveness Testing | Laboratory I.D. | HK1539570-005 | HK1539570-002 | HK1539570-003 | HK1539570-004 |
|---|---|---|---|---|---|
| | Date of Sampling & Testing | 29/10/2015 | 14/10/2015 | 29/10/2015 | 29/10/2015 |
| | SAMPLE IDENTIFICATION | Bared Au/Si wafer - Ref | Antibacterial coating (as treated) on Au/Si | Antibacterial coating (2000x rub) on Au/Si | Antibacterial coating (10000x rub) on Au/Si |
| | Unit: | % | % | % | % |
| | LOR | 0.1 | 0.1 | 0.1 | 0.1 |
| Test Organism Species *Escherichia coli* (AATCC 25922) | 1 | reduction rate after 1 hour | reduction rate after 1 hour | reduction rate after 1 hour | reduction rate after 1 hour |
| | | 12.5% | >99.9% | 41.5% | 30.0% |

Figure 3

Table 1

| Antimicrobial Effectiveness Testing | Laboratory I.D. | HK1539573-001 | | | | | | | | | |
|---|---|---|---|---|---|---|---|---|---|---|---|
| | Date of Sampling & Testing | 14/10/2015 | | | | | | | | | |
| | SAMPLE IDENTIFICATION | Inoculum control | Bared Au/Si wafer | | | | | Antibacterial coating (as treated) on Au/Si | | | |
| | Unit | CFU/mL | CFU/cm² | CFU/cm² | Nil | Nil | % | CFU/cm² | Nil | Nil | % |
| | LOR | 1 | 25 | 25 | 0.01 | 0.01 | 0.1 | 25 | 0.01 | 0.01 | 0.1 |
| | | Initial | U0h (hour) | U24h (hour) | Log U0 | Log U24h | Reduction rate after 24 hour | 24 hour | At (log value) | antibacterial activity (log value) | Reduction rate after 24 hour |
| Test Organism Species | | | | | | | | | | | |
| Escherichia coli (AATCC 25922) | CFU/mL inoculum | 270,000 | 24,000 | 240 | 4.38 | 2.38 | 99.0% | <2.5 | <0.40 | >2.38 | >99.9% |

Table 2

| Antimicrobial Effectiveness Testing | Laboratory I.D. | HK1539573-005 | | | | | | HK1539573-003 | | | | HK1539573-004 | | | |
|---|---|---|---|---|---|---|---|---|---|---|---|---|---|---|---|
| | Date of Sampling & Testing | 29/10/2015 | | | | | | 29/10/2015 | | | | 29/10/2015 | | | |
| | SAMPLE IDENTIFICATION | Inoculum control | Bared Au/Si wafer - Ref | | | | | Antibacterial coating (2000x rub) on Au/Si | | | | Antibacterial coating (10000x rub) on Au/Si | | | |
| | Unit | CFU/mL | CFU/cm² | CFU/cm² | Nil | Nil | % | CFU/cm² | Nil | Nil | % | CFU/cm² | Nil | Nil | % |
| | LOR | 1 | 25 | 25 | 0.01 | 0.01 | 0.1 | 25 | 0.01 | 0.01 | 0.1 | 25 | 0.01 | 0.01 | 0.1 |
| | | Initial | U0h (hour) | U24h (hour) | Log U0 | Log U24h | Reduction rate after 24 hour | 24 hour | At (log value) | antibacterial activity (log value) | Reduction rate after 24 hour | 24 hour | At (log value) | antibacterial activity (log value) | Reduction rate after 24 hour |
| Test Organism Species | | | | | | | | | | | | | | | |
| Escherichia coli (AATCC 25922) | CFU/mL inoculum | 570,000 | 17,000 | 14,000 | 4.23 | 4.15 | 17.6% | 6,600 | 3.82 | 0.33 | 61.2% | 10,000 | 4.00 | 0.15 | 41.2% |

Remark:
1. "Reduction rate" = (culture count at 0 hour of Untreated sample - culture count at 24 hour of treated sample)×100% / culture count at 0 hour of Untreated sample - culture count at 24 hour of Untreated sample

Figure 4

| Antimicrobial Effectiveness Testing | Laboratory I.D. | HK1539573-005 | HK1539573-002 | HK1539573-003 | HK1539573-004 |
|---|---|---|---|---|---|
| | Date of Sampling & Testing | 29/10/2015 | 14/10/2015 | 29/10/2015 | 29/10/2015 |
| | SAMPLE IDENTIFICATION | Bared Au/Si wafer - Ref | Antibacterial coating (as treated) on Au/Si | Antibacterial coating (2000x rub) on Au/Si | Antibacterial coating (10000x rub) on Au/Si |
| | Unit | % | % | % | % |
| | LOR | 0.1 | 0.1 | 0.1 | 0.1 |
| Test Organism Species | | Reduction rate after 24 hour | Reduction rate after 24 hour | Reduction rate after 24 hour | Reduction rate after 24 hour |
| Escherichia coli (AATCC 25922) | | 17.6% | >99.9% | 61.2% | 41.2% |

Remark:
1. "Reduction rate after 24 hour" = (culture count at 0 hour of Untreated sample - culture count at 24 hour of treated sample) x100% / culture count at 0 hour of Untreated sample

Figure 5

Test Results :

Test Part Description :

| Specimen No. | SGS Sample ID | Description |
|---|---|---|
| SN1 | TAO15-042826.001 | Silvery grey/golden plated Si wafer |
| SN2 | TAO15-042826.002 | Silvery grey/golden metal layer on Si wafer |

Remarks :
    (1) 1 mg/kg = 0.0001%
    (2) MDL = Method Detection Limit
    (3) ND = Not Detected ( < MDL )
    (4) "-" = Not Regulated

American Society for Testing and Materials – ASTM F 2923-14 (as specified by clients) – Total Cadmium content in certain substrate materials of children's jewelry

Test Method : With reference to CPSC Test Method: CPSC-CH-E1002-08.3. Analysis was performed by ICP-OES.

| Test Item(s) | Unit | MDL | 001 |
|---|---|---|---|
| Cadmium (Cd) | mg/kg | 5 | ND |

Notes :
    (1) No migration of elements test(s) was(were) conducted due to the total content results do not exceed Relevant limits.

American Society for Testing and Materials - ASTM F 2923-14 (as specified by clients)-Soluble Heavy Metal in paint and surface-coating of children's jewelry

Test Method : With reference to ASTM F 2923-14, analysis was performed by ICP-OES.

| Test Item(s) | Unit | MDL | 001 |
|---|---|---|---|
| Soluble Antimony (Sb) | mg/kg | 5 | ND |
| Soluble Arsenic (As) | mg/kg | 2.5 | ND |
| Soluble Barium (Ba) | mg/kg | 10 | ND |
| Soluble Cadmium (Cd) | mg/kg | 5 | ND |
| Soluble Chromium (Cr) | mg/kg | 5 | ND |
| Soluble Mercury (Hg) | mg/kg | 5 | ND |
| Soluble Selenium (Se) | mg/kg | 10 | ND |

Figure 6

Notes :
(1) Results shown are of the adjusted analytical results
(2) Mass of trace amount of sample ID 001 = 58.8

American Society for Testing and Materials – ASTM F 2923-14 (as specified by clients)– Total Lead content in children's jewelry

Test Method :   With reference to CPSC Test Method: CPSC-CH-E1002-08.3. Analysis was performed by ICP-OES.

| Test Item(s) | Unit | MDL | *001* |
|---|---|---|---|
| Total Lead (Pb) | mg/kg | 20 | ND |

American Society for Testing and Materials –ASTM F 2923-14(as specified by clients) –Nickel release

Test Method :   Simulation of wear and corrosion - EN 12472:2005 + A1:2009, followed by extraction - EN 1811:2011+ AC: 2012. Analysis was performed by ICP-OES.

| Test Item(s) | Unit | MDL | 002 |
|---|---|---|---|
| Volume of Test Solution | ml | - | 2.00 |
| Sample Area | cm² | - | 1.96 |
| Nickel Release - Trial 1 | µg/cm²/week | 0.10 | ND |
| Nickel Release - Trial 2 | µg/cm²/week | 0.10 | ND |
| Nickel Release - Trial 3 | µg/cm²/week | 0.10 | ND |

Notes :
(1) As Nickel is found to be negative by CR 12471:2002, simulation of wear and corrosion by the EN 12472:2005 + A1:2009 is performed

Figure 7

Test Part Description :

| Specimen No. | SGS Sample ID | Description |
|---|---|---|
| SN1 | TAO15-042813.001 | Silvery grey/golden plated Si wafer |
| SN2 | TAO15-042813.002 | Silvery grey/golden metal layer on Si wafer |

Remarks :
    (1) 1 mg/kg = 0.0001%
    (2) MDL = Method Detection Limit
    (3) ND = Not Detected ( < MDL )
    (4) "-" = Not Regulated

American Society for Testing and Materials –ASTM F 2999-14(as specified by clients) – Total Lead content in adult's jewelry- Materials not otherwise classified

Test Method : With reference to CPSC Test Method: CPSC-CH-E1002-08.3. Analysis was performed by ICP-OES. With reference to CPSC Test Method: CPSC-CH-E1001-08.3. Analysis was performed by ICP-OES.

| Test Item(s) | Unit | MDL | 001 |
|---|---|---|---|
| Lead (Pb) | mg/kg | 20 | ND |

American Society for Testing and Materials –ASTM F 2999-14 (as specified by clients) –Total Cadmium content in certain substrate materials of adult's jewelry

Test Method : With reference to CPSC Test Method: CPSC-CH-E1002-08.3. Analysis was performed by ICP-OES.

| Test Item(s) | Unit | MDL | 001 |
|---|---|---|---|
| Cadmium (Cd) | mg/kg | 5 | ND |

Notes :
    (1) No migration of elements test(s) was(were) conducted due to the total content results do not exceed Relevant limits.

Figure 8

American Society for Testing and Materials –ASTM F 2999-14 (as specified by clients) –Soluble Heavy Metal in paint and surface-coating of adult's jewelry

Test Method : With reference to ASTM F 2999-14, analysis was performed by ICP-OES.

| Test Item(s) | Unit | MDL | *001* |
|---|---|---|---|
| Soluble Antimony (Sb) | mg/kg | 5 | ND |
| Soluble Arsenic (As) | mg/kg | 2.5 | ND |
| Soluble Barium (Ba) | mg/kg | 10 | ND |
| Soluble Cadmium (Cd) | mg/kg | 5 | ND |
| Soluble Chromium (Cr) | mg/kg | 5 | ND |
| Soluble Mercury (Hg) | mg/kg | 5 | ND |
| Soluble Selenium (Se) | mg/kg | 10 | ND |

Notes :
(1) Results shown are of the adjusted analytical results
(2) Mass of trace amount of sample ID 001 is 62.8 mg.

American Society for Testing and Materials –ASTM F 2999-14 (as specified by clients) –Nickel release

Test Method : Simulation of wear and corrosion - EN 12472:2005 + A1:2009, followed by extraction - EN 1811:2011+ AC: 2012. Analysis was performed by ICP-OES.

| Test Item(s) | Unit | MDL | *002* |
|---|---|---|---|
| Volume of Test Solution | ml | - | 2.00 |
| Sample Area | cm² | - | 1.96 |
| Nickel Release - Trial 1 | µg/cm²/week | 0.10 | ND |
| Nickel Release - Trial 2 | µg/cm²/week | 0.10 | ND |
| Nickel Release - Trial 3 | µg/cm²/week | 0.10 | ND |

Notes :
(1) As Nickel is found to be negative by CR 12471:2002 Clause 5.3.4, simulation of wear and corrosion by the EN 12472:2005 + A1:2009 is performed.

Figure 9

PROCESS FOR COATING OF ARTICLES

TECHNICAL FIELD

The present invention relates to a process for applying a coating to an article and a coated article therefrom. More particularly, the present invention provides a process for applying a coating to an article, such as a functional coating.

BACKGROUND OF THE INVENTION

In the coating of components or articles which require a coating to be applied to the surface thereof, techniques in the art include discharge and acceleration related techniques which use acceleration of ions or the like.

Within the art, by way of example, mechanical watch components or micro parts typically formed from metal based, silicon based and nickel phosphorous (Ni—P) based materials, may require coating.

Due to high precision and substrate material characteristics, conventional machining and electroplating on metal parts typically cannot meet the critical requirements for high precision and non-conductive based micro parts during fabrication.

Such micro parts can be fabricated by Micro-electromechanical System (MEMS) technology such as Deep Reactive-Ion Etching (DRIE) and Ultraviolet Lithography (Lithography), and Galvanoformung, Abformung (UV-LIGA). Due to the limitation of production capacity and surface finishing requirements for such techniques, methodologies such as sputtering, e-beam or the like may be used in micro part deposition. Within the art, sputtering based deposition techniques are used in MEMS fabrication. These may be controlled through the adjustment of power, DC/RF switch, duration and pressure, for example on film thickness, width, and uniformity control.

For conventional sputtering type deposition, it is typically performed under high value of vacuum, and samples or articles to be coated are fixed to a holder device by way of mechanisms such pressure type fixtures, prior to application of sputtering and introduction to a vacuum chamber or the like.

In such processes of the art, deficiencies exist including the presence of some uncoated blind areas on the samples or articles that pressure fixtures may cover during the sputtering deposition process, and that may cause non-uniformity of coating surface on the back side from the sputtering source. Further, any film or coating may be scratched off relatively easily through hard contact between contact film and pressing fixtures.

For components, samples and articles including those silicon based, difficulty may be experienced using deposition methods of the prior art for the purpose of accurate thickness control, including in nano-scale, as in some application all surfaces of micro parts may be required to be deposited with thin film simultaneously.

In other applications, it is required to apply very thin coatings to articles, such as articles formed from metals or metal alloys, whereby such coatings must withstand at least a nominal amount of abrasive impact without the costings being abraded or worn off the article.

Again, in such processes as known in the art, providing such coatings which may be aesthetic or functional and uniformity of thickness, often wear off, debond, or are of a non-uniform thickness

OBJECT OF THE INVENTION

It is an object of the present invention to provide a process for coating of articles, which overcomes or at least partly ameliorates at least some deficiencies as associated with the prior art.

SUMMARY OF THE INVENTION

In a first aspect, the present invention provides process of providing an antibacterial coating to the surface of an article, said process including the steps of:
(i) applying a layer of an antibacterial precursor layer to the surface of an article to which an antibacterial coating is to be applied, wherein said antibacterial precursor layer is a precursor from which the coating is to be formed; and
(ii) directing a neutral molecular hydrogen flux from a neutral molecular hydrogen flux emission source towards the surface of the article;
wherein upon impact of neutral hydrogen molecules on molecules at or on the surface of an article, the bonds of the antibacterial precursor layer are selectively ruptured, and wherein the selectively ruptured bonds cross-link with themselves or with other chemical moieties at said surface resulting an antibacterial coating being formed on the surface of the article.

In an embodiment of the invention, the selectively ruptured bonds any one or combination of C—H bonds and Si—H bonds the C—H bonds and Si—H.

The process may further include the step of applying at least a first layer precursor to the surface of the article prior to application, wherein the first layer precursor is applied to the surface of the article prior to application of the antibacterial layer precursor to the article and disposed between the surface of the article and the antibacterial layer precursor.

Upon neutral molecular hydrogen flux from the neutral molecular hydrogen flux emission source emission source being directed towards the surface of the article, bonds of the material of the first layer precursor are selectively ruptured and cross-link with other chemical moieties at the surface of the article.

The ruptured bonds of the antibacterial precursor layer cross-link with the first later upon neutral molecular hydrogen flux from the neutral molecular hydrogen flux emission source emission source being directed towards the surface of the article.

The first layer precursor forms a monolayer of molecules or layer of thickness on the molecular level on the surface of the article. The first layer precursor may form an optically transparent layer.

In an embodiment, the first layer precursor is formed from 11-Mercaptoundecanoic acid.

In a further embodiment, the first layer precursor is applied to the surface of the article by providing a first layer precursor solution of 11-Mercaptoundecanoic acid in solution, and whereby the article is dipped in the 11-Mercaptoundecanoic acid solution for a predetermined amount of time and removed wherein upon drying the first layer precursor is formed on the article, and preferably the first layer precursor solution 50 Mm 11-Mercaptoundecanoic acid in ethanol.

In another embodiment, the antibacterial precursor layer is provided by an antibacterial precursor solution including an antibacterial compound, and the antibacterial compound may be Chitosan.

The antibacterial precursor solution may be a solution including Chitosan, a polymer, an acid and a surfactant.

Preferably, the antibacterial precursor solution is formed from Chitosan, Polyquaternium-6, Acetic Acid, and Tween 20 in deionized water, and more preferably the antibacterial precursor solution is formed from Chitosan and Polyquaternium-6 in a ratio of about 1:1, Acetic Acid and about 0.005 wt % Tween 20 in deionized water.

The antibacterial coating applied to is preferably a monolayer of molecules or layer of thickness on the molecular level, and the antibacterial coating is preferably optically transparent.

In embodiments of the invention, the surface of the article may be formed from a metal or metal alloy; formed from a precious metal including those selected from the group including gold, gold based alloy, silver, platinum or the like; formed from formed from a polymeric material; or formed from formed from a silicon or silicon based material.

The article may be an item of jewellery, a timepiece component, medical devices, medical instruments, implants, hygiene instruments, containers, vessels, packaging materials or the like.

In a second aspect the present invention provides an article having an antibacterial coating applied thereto, wherein the antibacterial coating is applied to the article according to the process according to the first.

In a third aspect, the present invention provides a process of providing a coating layer on the surface of an article, said process including the steps of:
(i) applying a first layer precursor to the surface of the article;
(ii) applying an outer layer precursor to the article over said first layer precursor; and
(ii) directing a neutral molecular hydrogen flux from a neutral molecular hydrogen flux emission source towards the surface of the article;
  wherein upon impact of neutral hydrogen molecules on molecules at or on the surface of an article, the bonds of the first precursor layer are selectively ruptured and wherein the selectively ruptured bonds cross-link with at least of other chemical moieties at said surface resulting in a first layer being formed on the surface of the article; and
  wherein upon impact of neutral hydrogen molecules on molecules at or on the surface of an article, the bonds of the outer layer precursor layer are selectively ruptured and wherein the selectively ruptured bonds cross-link with at least other chemical moieties of the first layer resulting in a coating layer being formed on the article.

In an embodiment, the selectively ruptured bonds any one or combination of C—H bonds and Si—H bonds the C—H bonds and Si—H.

In a further embodiment, the outer layer precursor includes an antibacterial compound such that the coating layer is an antibacterial coating.

In another embodiment, the outer layer precursor includes an anti-wetting compound such that the coating layer is an anti-wetting coating.

The first layer is preferably a monolayer of molecules or layer of thickness on the molecular level, such that upon cross linking the first layer is optically transparent.

Preferably, the coating layer is a monolayer of molecules or layer of thickness on the molecular level, such that upon cross linking the coating layer is optically transparent.

In a fourth aspect, the present invention provides an article having a coating layer applied thereto, wherein the coating layer is applied to the article according to the process according to the third aspect.

BRIEF DESCRIPTION OF THE DRAWINGS

An example of the invention will now be described with reference to the accompanying drawings, in which:

FIG. 2 shows results for antibacterial assessment by ASTM E2149 Standard for articles having an antibacterial coating applied to a gold surface; at one hour post inoculation with bacteria;

FIG. 3 shows a summary of the results of FIG. 2;

FIG. 4 shows results for antibacterial assessment by International Standard ISO22196 for articles having an antibacterial coating applied to a gold surface; at 24 hours post inoculation with bacteria;

FIG. 5 shows a summary of the results of FIG. 4;

FIG. 6 shows results for jewellery toxicity in accordance with ASTM F 2923-14—Total Cadmium content in certain substrate materials of children's jewelry; and ASTM F 2923-14—Soluble Heavy Metal in paint and surface-coating of children's jewelry;

FIG. 7 shows results for jewellery toxicity in accordance with ASTM F 2923-14—Total Lead content in children's jewelry; and ASTM F 2923-14—Nickel release;

FIG. 8 shows results for jewellery toxicity in accordance with ASTM F 2000-14—Total Lead content in adult's jewelry; and ASTM F 2999-14—Total Cadmium content in certain substrate materials of adult's jewelry; and FIG. 9 shows results for jewellery toxicity in accordance with ASTM F 2999-14—Soluble Heavy Metal in paint and surface-coating of adults' jewelry; and ASTM F 2999-14—Nickel release

DETAILED DESCRIPTION OF THE DRAWINGS

Figure 1:
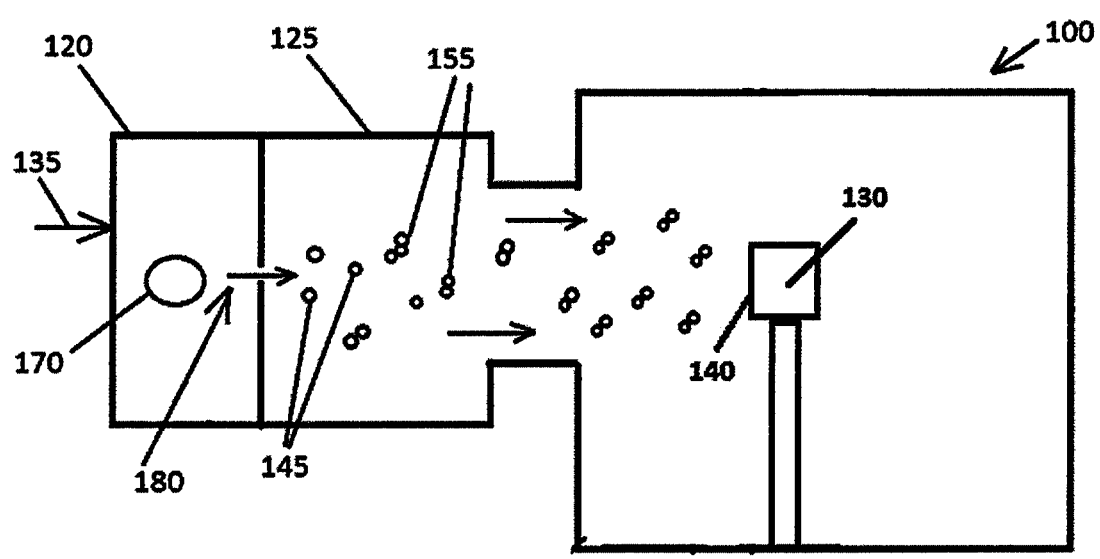
FIG. 1 shows a schematic representation of an embodiment of a system for the application of a coating to an article according to the present invention.

The present invention provides a process for the application of a coating to the surface of an article, whereby very thin coatings, to the order of the molecular level, may formed on the surface of an article.

In embodiments of the invention, the invention provides for an antibacterial coating which is applicable for application to articles of jewellery, providing health benefits to persons wear such articles of jewellery. In such applications, it is paramount that the article's optical appearance is not altered, the present invention is particularly applicable. The present invention provides a coating which is optically transparent, and it's impossible to detect by observation, and indication exists that such a coating is present.

Furthermore, in applications such as jewellery, it is required that the coating not be readily abraded or worn off the article in normal usage and as such, a coating applicable to jewellery, as provided by the present invention, must be resistive to such wear.

Other coatings as provided by the present invention, such anti-wetting coating, may also be applied in a layer of the molecular level, so that light may be transmitted therethrough without any indication that a coating exits. As such a coating is extremely thin and in the molecular range, it is important that the coating is well adhered or attached to an article, and the coating is resistive to typically applicable wear, for example when applied to In order to provide such a coating process, the present inventors have utilized a neutral molecular hydrogen flux emission source which is directed towards an article which has been pre-treated by applying precursor coating to the article, which upon having the neutral molecular hydrogen flux applied thereto forms a coating.

For use in the present invention, such a neutral molecular hydrogen flux can be provided in a manner as described in U.S. Pat. No. 9,113,544, from application Ser. No. 13/255,038 to Lau, W. M. Leo et at, and which is hereby incorporated by way of cross-reference.

The manner in which the neutral molecular hydrogen flux can be provided in order to provide a coating on the surface of an article, includes the steps of:
(a) forming a plasma and extracting from said plasma a flux of protons having energies in a range from about 50 eV to about 1 key; thereafter
(b) directing the flux of protons into a chamber and introducing molecules of hydrogen into the chamber;
(c) imparting kinetic energy to said molecules of hydrogen by colliding the protons from said flux of protons with the molecules of hydrogen to produce energetic hydrogen molecules;
(d) producing a flux of neutral molecular hydrogen having kinetic energies in a range from about 1 eV to about 100 eV by cascading collisions between said energetic hydrogen molecules and other hydrogen molecules resulting in all directional scattering of the energetic hydrogen molecules; and
(e) directing the flux of neutral molecular hydrogen to the substrate surface such that upon impact of neutral hydrogen molecules on molecules at or on the surface containing any one or combination of C—H bonds and Si—H bonds the C—H bonds and Si—H bonds are selectively ruptured.

Upon collision of the neutral molecular hydrogen with the precursor layer, the selectively ruptured bonds cross-link with themselves or with other chemical moieties at the surface resulting in a change in surface properties, or a combination thereof.

Referring to FIG. 1, there is shown a schematic representation of a system 100 of the manner in which a coating according to the present invention may be applied to an article. In the present embodiment, the emission source 120 is a neutral molecular hydrogen flux emission source and the emission elements are neutral molecular hydrogen 155.

The neutral molecular hydrogen flux emission source 120 directs a flux of neutral molecular hydrogen 155 towards the support member 110, such that upon impact of neutral hydrogen molecules 155 on molecules at or on the surface 140 of an article 130, bonds between elements of the molecules at or on the surface 140 of an article 130 electively ruptured.

The neutral molecular hydrogen flux emission source 120 includes a hydrogen plasma source 170, with hydrogen gas 130 delivered to the hydrogen flux emission source 120, and hydrogen plasma 145 is accelerated to chamber 125, and neutral molecular hydrogen flux emission 155 is directed towards the article 130.

The hydrogen plasma source 170 may be a plasma source selected from the group including a DC plasma, an RF plasma, an ordinary microwave plasma, or an electron cyclotron resonance (ECR) microwave plasma.

In an embodiment applicable to the present invention, the neutral molecular hydrogen flux emission source 120 directs a flux of neutral molecular hydrogen 155 having kinetic energies in a range from about 1 eV to about 100 eV towards the support member 110, such that upon impact of neutral hydrogen molecules on molecules at or on the surface of an article containing any one or combination of C—H bonds and Si—H bonds the C—H bonds and Si—H bonds are selectively ruptured.

The provision of a neutral molecular hydrogen flux emission flux for the breaking of bonds as utilized in the present invention, be provided by the steps as follows for the breaking any one or combination C—H and Si—H molecular bonds in molecules at or on a surface of the article.

The process of the present invention utilizes the above process in order to provide requisite coatings.

As will appreciated by those skilled in the art, the chemical reactions in the above described bond breaking and cross-linking processes as utilized in the present invention is complex, and numerous parameters are required to be considered, including control of the amount of neutral molecular hydrogen flux emission flux, energy levels, power, materials at the surface of the article, materials properties from which the precursor material is formed in order to form the coating, chemical and physical properties of the precursor material which forms the coating, functional attributes and biological attributes of a precursor material for forming an antibacterial coating, wear related properties, application and thickness of precursor layer and the like.

An example of an antibacterial coating process and application thereof and in accordance with the present invention, is described as follows.

1. Example—Antibacterial Coating System and Materials

In accordance with the present invention, an antibacterial coating system is provided for application of an antibacterial coating to the surface of an article formed from gold whereby the outer surface upon which the coating is applied if formed from gold.

In order to provide an antibacterial coating to such an article in the present example, the process includes the following main steps:
(i) applying a first layer precursor to the surface of the article;
(ii) applying an antibacterial precursor layer to the article over said first layer precursor; and
(iii) directing a neutral molecular hydrogen flux from a neutral molecular hydrogen flux emission source towards the surface of the article.

1.1 First Layer Precursor

The first later precursor in the present example is applied to the article by way of a first solution which is comprised of 50 Mm 11-Mercaptoundecanoic acid in ethanol.

The article is dipped in the first solution at an elevated temperature of about 35 degrees Celsius for a time interval of about 10 minutes.

The article is then removed from the first solution and rinsed in ethanol.

As will be appreciated, depending upon the articles to be coated the above parameters may require some alteration.

The article is then dried for example by way of a blow dryer until dry, following which the antibacterial precursor layer is applied to the article.

1.2 Antibacterial Layer Precursor

In order to apply the antibacterial precursor layer to the article, which is to be applied on the first layer precursor, the antibacterial precursor layer is applied by way of a second solution which includes an antibacterial compound.

In the present example, the antibacterial compound is Chitosan, and the second solution is comprised of Chitosan and Polyquaternium-6 in a ratio of about 1:1, Acetic Acid and about 0.005 wt % Tween 20 in deionized water.

The article is dipped in the second solution for about 60 seconds, after which the sample is removed at relative moderate linear speed of about 2000 micrometre/second. This dipping and removal process is repeated a number of times, for example five times.

As will be appreciated, depending upon the articles to be coated the above parameters may require some alteration.

Upon completion of the dipping and removal process, the article is dried at an elevated temperature of about 45 degrees Celsius for about 15 minutes, and the antibacterial coating precursor is thereby formed.

1.3 Neutral Molecular Hydrogen Flux Exposure

Upon completion of formation of the antibacterial coating precursor, the article is then exposed to a neutral molecular hydrogen flux, for ex ample as described in reference to FIG. 1, whereby impact of neutral hydrogen molecules, the bonds of the first precursor layer are selectively ruptured and wherein the selectively ruptured bonds cross-link with at least other chemical moieties at the surface resulting in a first layer being formed on the surface of the article.

The impact of neutral hydrogen molecules on molecules causes the bonds of the antibacterial precursor layer to be selectively ruptured, wherein the selectively ruptured bonds cross-link with at least other chemical moieties of the first layer resulting in an antibacterial coating layer being formed on the gold article.

The article is exposed to the neutral molecular hydrogen flux in accordance with the invention, by way of example in the manner as described with reference to FIG. 1.

The effectiveness of the above example was evaluated using standard testing and analysis protocol as described as follows.

2. Antibacterial Assessment

In order to assess the antibacterial effectivity of the antibacterial coating as provided by the present invention when applied to a gold substrate, independent testing laboratory analysis was conducted utilizing international standards as follows.

2.1 Bacterial Activity after 1 Hour

Tests were conducted under ASTM E2149 Standard "Determining the Antimicrobial Activity of Immobilized Antimicrobial Agents Under Dynamic Contact Condition" in order to determine the effectiveness of the antibacterial coating after one hour after exposure to bacteria.

Silicon wafer samples for analysis having a gold layer thereon, whereby the gold layer was coated with an antibacterial coating using the antibacterial system as described with reference to Example 1 above, and subjected to exposure to a neutral molecular hydrogen flux by an apparatus utilizing the process as described with reference to FIG. 1 and owned by the present applicant, which utilizes microwave power.

Five samples were provided to the testing laboratory, three with an antibacterial coating applied thereto, and two for control testing.

Samples were inoculated with a suspension containing *Escherichia Coli* (AATCC 25922) at colony-forming unit/mL (CFU/mL) as follows:
(i) Initial CFU/mL of 270,000 of untreated sample vs. treated sample, and
(ii) Initial CFU/mL of 170,000,000 of untreated sample vs. coated sample at 2000× rub and coated sample at 10000× rub.

The results as provided by the analysis laboratory are reproduced in FIG. 2, and a summary of the results after one hour is reproduced in FIG. 3.

As is shown by FIG. 3, after one hour, for when a sample having an antibacterial coating which was not exposed to a rubbing, there was a reduction in bacteria of greater than 99.9%.

For samples having an antibacterial coating and rub of 2000× and 10000×, there was a reduction in bacteria of 41.5% and 30.5% respectively.

2.2 Bacterial Activity after 24 Hours

Tests were conducted under International Standard ISO22196 "Measurement of antibacterial activity on plastics and other non-porous surfaces"," in order to determine the effectiveness of the antibacterial coating after 24 hours after exposure to bacteria.

Silicon wafer samples for analysis having a gold layer thereon, were coated with an antibacterial coating using the antibacterial system as described with reference to Example 1 above, and subjected to exposure to a neutral molecular hydrogen flux by an apparatus utilizing the process as described again with reference to FIG. 1 and owned by the present applicant.

Five samples were provided to the testing laboratory, three with an antibacterial coating applied thereto, and two for control testing.

Samples were inoculated with a suspension containing *Escherichia Coli* (AATCC 25922) at colony-forming unit/mL (CFU/mL), with 0.4 ml of inoculum used for each sample as follows:
(i) Initial CFU/mL of 270,000 of untreated sample vs. treated sample, and
(ii) Initial CFU/mL of 570,000,000 of untreated sample vs. coated sample at 2000× rub and coated sample at 10000× rub The results as provided by the analysis laboratory are reproduced in FIG. 4, and a summary of the results after 24 hours is reproduced in FIG. 5.

As is shown by FIG. 5, after 24 hours, for when a sample having an antibacterial coating which was not exposed to a rubbing, there was a reduction in bacteria of greater than 99.9%.

For samples having an antibacterial coating and rub of 2000× and 10000×, there was a reduction in bacteria of 61.2% and 41.2% respectively.

2.3 Conclusions from Antibacterial Assessment

The results of both tests, at 1 hour and 24 hours post inoculation with bacteria, demonstrated that the antibacterial coating as provided by the present invention, when applied to an article having a gold surface and without any rub, substantially killed all bacteria.

For samples for which a rub was applied, the antibacterial coating significantly reduced the amount of bacteria both after 1 hour and 24 hours.

The results demonstrated that although the antibacterial coating has a thickness only of the molecular level, the antibacterial coating when applied to a gold article such as an item of jewellery which is exposed to wear, still significantly reduces the amount of bacteria on the surface of the article.

Accordingly, the present invention provides an antibacterial coating suitable for application to articles of jewellery, such as those formed from gold.

Although in the present example, Chitosan is utilised as an antibacterial agent, other antibacterial agents may be utilised in other examples and within the scope of the present invention.

3. Jewellery Article Applicability Assessment

In order to demonstrate the applicability of the antibacterial coating of the present invention and standards compliance for articles of jewellery, gold coated articles were assessed and analysed in respect of the irrelevant standards, for both children and adult's jewellery.

3.1 Children's Jewellery Applicability Assessment

Antibacterial coatings applied to gold on silicon wafers whereby the antibacterial coatings were applied to the gold surface, were assessed by an external testing organization, in respect of the following standards:
(i) ASTM F 2923-14—Total Cadmium content in certain substrate materials of children's jewelry
(ii) ASTM F 2923-14—Soluble Heavy Metal in paint and surface-coating of children's jewelry
(iii) ASTM F 2923-14—Total Lead content in children's jewelry
(iv) ASTM F 2923-14—Nickel release Referring to FIGS. 6 and 7, the results of the test as provided are reproduced. As is demonstrated, no elements were found in any of the coated samples, whereby each test returned "ND" which means the elements were "Not Detected", which is denoted when the amount of an element is less than the Method Detection Limit.

3.2 Adult's Jewellery Applicability Assessment

Antibacterial coatings applied to gold on silicon wafers whereby the antibacterial coatings were applied to the gold surface, were assessed by an external testing organization, in respect of the following standards:
(i) ASTM F 2000-14—Total Lead content in adult's jewelry
(ii) ASTM F 2999-14—Total Cadmium content in certain substrate materials of adults' jewelry
(iii) ASTM F 2999-14—Soluble Heavy Metal in paint and surface-coating of adults' jewelry
(iv) ASTM F 2999-14—Nickel release Referring to FIGS. 8 and 9, the results of the test as provided are reproduced. As is demonstrated, no elements were found in any of the coated samples, whereby each test returned "ND" which means the elements were "Not Detected", which is denoted when the amount of an element is less than the Method Detection Limit.

3.3 Jewellery Article Applicability Assessment

The results of analysis demonstrated that gold articles having an antibacterial coating according to the present invention have no detectable elements which may by toxic, from the standard jewelry testing standards, and are thus in compliance with the standards requirements for jewellery.

As such, the present invention provides an antibacterial coating applicable to jewellery articles for both children and adults.

4. Applicability of Antibacterial Coating for Jewellery

Articles of jewellery are constantly in contact with the skin of a person and as such, the presence of bacteria thereon poses health risks and concerns. In particular, children may inadvertently transfer bacteria present on the surface of an article of jewellery to their mouths, which poses further health risks. Further, as some articles of jewellery extend through the dermis of person, for example ear rings for pierced ears, there is increased risk of bacterial infection from bacteria present on the jewellery.

Further, as some articles of jewellery, such as finger rings, are on or adjacent the hand of a person, in daily use and contact with object and other persons, bacteria may be transferred to the article of jewellery, exposing the wearer at risk. Articles of jewellery, such as ginger rings, often have ornate have an ornate structure and geometry, which includes recesses and rebates and areas difficult to access, such as the region about a gemstone setting, providing sites for the hosting and growth of bacteria. Due to the nature of jewellery, users are often reluctant to clean jewellery articles on a very regular basis, and in the event of hand washing articles of jewellery such as finger rings may not be thoroughly cleaned and retain bacteria.

Accordingly, there is an inherent need from a hygiene and safety standpoint, for reduction of the risk of exposure to bacteria on articles of jewellery.

Unlike many other articles to which antibacterial coatings may be required, articles of jewellery have the specific requirements of such an antibacterial coating:
(i) it must have suitable potency for the killing and reduction of bacteria if exposed to bacteria,
(ii) it must be optically invisible, and not detract from any aesthetic effects that an article of jewellery has, such as alteration of the optical properties of gold for articles of jewellery formed from gold,
(iii) It must not provide any alteration in tactile sensation when applied to jewellery, as a user must experience the same tactile sensation as to an untreated material, so as not to detract from the value and physical expectations of a person,
(iv) it must be able to withstand normal wear and tear on a daily basis, as there is inherently abrasion and wear to a surface of an article of jewellery during use,
(v) it must comply with standards, and the processing and process used in the application of the coating to an article of jewellery must not cause any alteration in chemical structure of the coating or the substrate of the article to which it is to be applied, which would cause potentially toxic elements or compounds to be released, and be in compliance with the relevant jewellery standards, and it must not have any potentially toxic elements or compounds, and be in compliance with the relevant jewellery standards,
(vi) the process utilised to apply the coating must not cause any damage to the surface of the article of jewellery, and
(vii) it should be able to be re-applied when ultimately worn off the surface of the article, or when damaged.

As demonstrated above, the present invention provides an antibacterial coating suitable for use on the surface of articles of jewellery and satisfies the above recited requirements as follows:
(1) effectivity of action against bacteria has been demonstrated and independently evaluated,
(2) by applying the coating as a monolayer or on the molecular level, the coating is not discernable to the naked eye, and the presence thereof requires scientific analytical techniques,
(3) due to the coating being applied as such a thin layer and the materials thereof, its presence is impossible to be detected by way of feeling, and as such provides not tactile alteration at all,
(4) Standards tests demonstrated the although the coating is applied in extremely small amounts, upon being exposed to large amounts of wear, the coating remained effective against bacteria,
(5) Compliance with jewellery toxicity assessment standards has been demonstrated and independently evaluated,
(6) The process of the present invention requires no surface alteration for the application of the antibacterial coating, and
(7) the process of the present invention be re-applied to articles for which an antibacterial coating has been removed or abraded therefrom.

The present invention, in preferred embodiments, provides a process for forming an antibacterial coating on the surface of an article, which overcome deficiencies and shortcomings in the prior art.

Solutions of the prior art do not provide a uniform coating, in particular for articles which require very thin film coatings, with deficiencies including variation in optical aspects of the article due to non-uniformity, insufficient "wrap around" whereby the coating does not extend appropriately around an edge of an article giving rise to peeling and debonding of the coating from the article.

Furthermore, solutions of the prior art do not allow for very thin coatings to be readily applied to articles when such a coating is required to be optically transparent.

The present invention provides solutions to the deficiencies of the prior art by providing a process which enables a more uniform and well bonded coating to be applied to an article.

Other deficiencies of the prior art are that there is minimal deposition or coating formation on the edges of the articles, which provides for an aesthetically inferior product, resulting in lower yield and increased inspection time and determination of fulfillment of design requirements.

Furthermore, such techniques of the prior art result in articles with susceptibility for a coating to flake off or debond from the article, due to the thin coating and lack of "wrap-around" to the edges adjacent the surface to which the coating is applied to the articles, resulting in lower yield and increased inspection time and determination of fulfillment of design requirements. This also may result in failure after a period of time, having detrimental commercial effects.

Still further, such prior art techniques require removal of the articles from a substrate to which they are placed, which may compromise the integrity of the coating and create some peeling, again resulting in lower yield and increased inspection time and determination of fulfillment of design requirements.

Although within the examples, Chitosan is utilised as an antibacterial agent, other antibacterial agents may be utilised in other examples and within the scope of the present invention.

Whilst the examples as provided are directed to application of an antibacterial coating to a gold surface, in particularly with reference to applicability to articles of jewellery. However, as will be appreciated by those skilled in the art, the invention is also applicable to formation of thin coatings, for example ant-wetting coatings.

In other or alternate embodiments, the present invention and process thereof, the article may be formed from a metal or metal alloy, formed from a precious metal including gold based allow, silver, platinum or the like, or formed from a polymeric material; or formed from formed from a silicon or silicon based material.

Other articles applicable to such coatings include timepiece components, medical devices, medical instruments, implants, hygiene instruments, containers, vessels, packaging materials or the like.

The invention claimed is:

1. A process of providing an antibacterial coating to a surface of an article, said process including the steps of:
   (i) applying a layer of an antibacterial precursor layer to the surface of an article to which an antibacterial coating is to be applied, wherein said antibacterial precursor layer is a precursor from which the coating is to be formed; and
   (ii) directing a neutral molecular hydrogen flux from a neutral molecular hydrogen flux emission source towards the surface of the article;
   wherein upon impact of neutral hydrogen molecules on molecules at or on the surface of an article, the bonds of the antibacterial precursor layer are selectively ruptured, and wherein the selectively ruptured bonds cross-link with themselves or with other chemical moieties at said surface or a combination thereof, resulting an antibacterial coating being formed on the surface of the article,
   wherein the process further includes the step of applying at least a first layer precursor to the surface of the article, wherein the first layer precursor is applied to the surface of the article prior to application of the antibacterial layer precursor to the article and disposed between the surface of the article and the antibacterial layer precursor, and
   wherein the first layer precursor is formed from 11-Mercaptoundecanoic acid, and wherein the first layer precursor is applied to the surface of the article by providing a first layer precursor solution of 11-Mercaptoundecanoic acid in solution, and whereby the article is dipped in the 11-Mercaptoundecanoic acid solution for a predetermined amount of time and removed wherein upon drying the first layer precursor is formed on the article.

2. The process according to claim 1, wherein the selectively ruptured bonds any one or combination of C—H bonds, Si—H bonds.

3. The process according to claim 1, wherein upon neutral molecular hydrogen flux from the neutral molecular hydrogen flux emission source being directed towards the surface of the article, bonds of the material of the first layer precursor are selectively ruptured and cross-link with other chemical moieties at the surface of the article.

4. The process according to claim 1, wherein ruptured bonds of the antibacterial precursor layer cross-link with the first layer upon neutral molecular hydrogen flux from the neutral molecular hydrogen flux emission source being directed towards the surface of the article.

5. The process according to claim 1, wherein the first layer precursor forms a monolayer on the surface of the article.

6. The process according to claim 1, wherein the first layer precursor forms an optically transparent layer.

7. The process according to claim 1, wherein the first layer precursor solution is 50 Mm 11-Mercaptoundecanoic acid in ethanol.

8. The process according to claim 1, wherein the antibacterial precursor layer is provided by an antibacterial precursor solution including an antibacterial compound.

9. The process according to claim 1, wherein the antibacterial compound is Chitosan.

10. The process according to claim 8, wherein the antibacterial precursor solution is a solution including Chitosan, a polymer, an acid and a surfactant.

11. The process according to claim 8, wherein the antibacterial precursor solution is formed from Chitosan, Polyquaternium-6, Acetic Acid, and Tween 20 in deionized water.

12. The process according to claim 8, wherein the antibacterial precursor solution is formed from Chitosan and Polyquaternium-6 in a ratio of about 1:1, Acetic Acid and about 0.005 wt % Tween 20 in deionized water.

13. The process according to claim 1, wherein the antibacterial coating applied to is a monolayer of molecules or layer of thickness on the molecular level.

14. The process according to claim 1, wherein the antibacterial coating is optically transparent.

15. The process according to claim 1, wherein the surface of the article is formed from a metal or metal alloy,
- wherein the surface of the article is formed from a precious metal including those selected from the group including gold, gold based alloy, silver, platinum or the like,
- wherein the surface of the article is formed from a polymeric material, or wherein the surface of the article is formed from a silicon or silicon based material,
- wherein the surface of the article is formed from a silicon or silicon based material.

16. The process according to claim 1, wherein the article is an item of jewellery,
- wherein the article is a timepiece component,
- wherein the article is a medical device, medical instrument, implant, hygiene instrument or the like, or
- wherein the article a container, vessel, packaging material or the like.

17. An article having an antibacterial coating applied thereto, wherein the antibacterial coating is applied to the article according to the process according to claim 1.

* * * * *